United States Patent [19]

Chang et al.

[11] Patent Number: 4,808,536

[45] Date of Patent: Feb. 28, 1989

[54] IMMUNOCHEMICAL METHOD FOR DETECTION OF ANTIBODY AGAINST HTLV-III CORE PROTEIN BASED UPON RECOMBINANT HTLV-III GAG GENE ENCODED PROTEIN

[75] Inventors: Nancy T. Chang, Houston, Tex.; John Ghrayeb, Thorndale, Pa.

[73] Assignee: Centocor, Inc., Malvern, Pa.

[21] Appl. No.: 834,212

[22] Filed: Feb. 27, 1986

[51] Int. Cl.[4] ................ G01N 33/545; B65D 69/00; C12Q 1/70

[52] U.S. Cl. ........................... 435/5; 424/89; 435/7; 435/810; 436/811; 436/808; 530/300; 530/324; 530/350; 530/403; 530/826

[58] Field of Search ............... 435/517, 810; 436/808; 530/300, 324, 350, 403, 826; 424/89

[56] References Cited

U.S. PATENT DOCUMENTS 4,520,113  5/1985  Gallo et al. .................. 436/504
4,629,783  12/1986  Cosand ........................ 530/324
4,661,445  4/1987  Saxinger .
4,689,398  8/1987  Wu et al. .

FOREIGN PATENT DOCUMENTS

85/04903  11/1985  PCT Int'l Appl. .............. 435/5

OTHER PUBLICATIONS

Casey, J. M. et al., *J. Virol.* 55 (2), 417–423 (1985).
Kalyanaraman, V. S. et al., *Science* 225, 321–323.
Neurath, A. R. et al., *J. Immunol. Med.* 11, 75–86.
Chang et al., *Biotechnology* 3, 905–909 (1985).
Sarngadharan et al., *Science* 224, 506–508 (1984).
Dowbenko, D. J. et al. (1985) *Proc. Natl. Acad. Sci. U.S.A.* 82:7748.
Crowl, R., et al., *Cell*, 41, 979–986 (1985).
Carbradilla, C. D., et al., *Biotechnology*, 4, 128–133 (1986).
Chang et al, *Science*, vol. 228 (Apr. 5, 1985) 93–96.

*Primary Examiner*—Christine M. Nucker
*Attorney, Agent, or Firm*—Hamilton, Brook, Smith & Reynolds

[57] ABSTRACT

Immunochemical assays for detection of antibodies against HTLV-III core proteins are described. The assays are based upon recombinant HTLV-III core proteins expressed by cloned DNA segments of the gag region of the HTLV-III genome. Immunoreactive, chimeric HTLV-III core proteins and methods of producing these proteins are also described.

21 Claims, 4 Drawing Sheets

```
                                                              GCAGAATGGGAT
                                                              AlaGluTrpAsp    4
AGAGTACATCCAGTGCATGCAGGGCCTATTGCACCAGGCCAGATGAGAGAACCAAGGGGAAGTGACATAGCAGGA
ArgValHisProValHisAlaGlyProIleAlaProGlyGlnMetArgGluProArgGlySerAspIleAlaGly  29

ACTACTAGTACCCTTCAGGAACAAATAGGATGGATGACAAATAATCCACCTATCCCAGTAGGAGAAATTTATAAA
ThrThrSerThrLeuGlnGluGlnIleGlyTrpMetThrAsnAsnProProIleProValGlyGluIleTyrLys  54

AGATGGATAATCCTGGGATTAAATAAAATAGTAAGAATGTATAGCCCTACCAGCATTCTGGACATAAGACAAGGA
ArgTrpIleIleLeuGlyLeuAsnLysIleValArgMetTyrSerProThrSerIleLeuAspIleArgGlnGly  79

CCAAAAGAACCTTTTAGAGACTATGTAGACCGTTCTATAAAACTCTAAGAGCCGAGCAAGCTTCACAGGAGGTA
ProLysGluProPheArgAspTyrValAspArgPheTyrLysThrLeuArgAlaGluGlnAlaSerGlnGluVal  104
                                                                   |B
AAAAATTGGATGACAGAAACCTTGTTGGTCCAAAATGCGAACCCAGATTGTAAGACTATTTTAAAAGCATTGGGA
LysAsnTrpMetThrGluThrLeuLeuValGlnAsnAlaAsnProAspCysLysThrIleLeuLysAlaLeuGly  129

CCAGCGGCTACACTAGAAGAAATGATGACAGCATGTCAGGGAGTAGGAGGACCCGGCCATAAGGCAAGAGTTTTG
ProAlaAlaThrLeuGluGluMetMetThrAlaCysGlnGlyValGlyGlyProGlyHisLysAlaArgValLeu  154

GCTGAAGCAATGAGCCAAGTAACAAATACAGCTACCATAATGATGCAGAGAGGCAATTTTAGGAACCAAAGAAAG
AlaGluAlaMetSerGlnValThrAsnThrAlaThrIleMetMetGlnArgGlyAsnPheArgAsnGlnArgLys  179

ATGGTTAAGTGTTTCAATTGTGGCAAAGAAGGGCACACAGCCAGAAATTGCAGGGCCCCTAGGAAAAAGGGCTGT
MetValLysCysPheAsnCysGlyLysGluGlyHisThrAlaArgAsnCysArgAlaProArgLysLysGlyCys  204

TGGAAATGTGGAAAGGAAGGACACCAAATGAAAGATTGTACTGAGAGACAGGCTAATTTTTTAGGGAAGATC
TrpLysCysGlyLysGluGlyHisGlnMetLysAspCysThrGluArgGlnAlaAsnPheLeuGlyLysIle   228
                                                                      |A
```

FIGURE 5

```
                                                                    GCAGAATGGGAT
                                                                    AlaGluTrpAsp    4

AGAGTACATCCAGTGCATGCAGGCCTATTGCACCAGGCCTAGTGAGAGAACCAAGGGAAGTGACATAGCAGGA
ArgValHisProValHisAlaGlyProIleAlaProGlyMetArgGluProArgGlySerAspIleAlaGly     29

ACTACTAGTACCCTTCAGGAACAGATAGGATGGATGACAAATAATCCACCTATCCCAGTAGGAGAAATTTATAAA
ThrThrSerThrLeuGlnGluGlnIleGlyTrpMetThrAsnAsnProProIleProValGlyGluIleTyrLys     54

AGATGGATAATCCTGGATTAAATAAAATAGTAAGAATGTATAGCCCTACCAGCATTCTGGACATAAGACAAGGA
ArgTrpIleIleLeuGlyLeuAsnLysIleValArgMetTyrSerProThrSerIleLeuAspIleArgGlnGly     79

CCAAAAGAACCTTTTAGAGACTATGTAGACCGGTTCTATAAAACTCTAAGAGCCGAGCAAGCTTCACGGAGGTA
ProLysGluProPheArgAspTyrValAspArgPheTyrLysThrLeuArgAlaGluGlnAlaSerGlnGluVal    104
                                                                              B

AAAAATTGGATGACAGAAACCTTGTTGGTCCAAATGGAACCCAGATTGTAAGACTATTTTAAAAGCATTGGGA
LysAsnTrpMetThrGluThrLeuLeuValGlnAsnAlaAsnProAspCysLysThrIleLeuLysAlaLeuGly    129

CCAGGCGCTACACTAGAGAAATGATGACAGCATGTCAGGGAGTAGGAGGACCCGGCCATAAGGCAAGAGTTTTG
ProAlaAlaThrLeuGluGluMetMetThrAlaCysGlnGlyValGlyGlyProGlyHisLysAlaArgValLeu    154

GCTGAAGCAATGAGCCAAGTAACAAATACAGCTACCATAATGATGCAGAGAGGCAATTTTAGGAACCAAAGAAAG
AlaGluAlaMetSerGlnValThrAsnThrAlaThrIleMetMetGlnArgGlyAsnPheArgAsnGlnArgLys    179

ATGGTTAAGTGTTTCAATTGTGGCAAAGAAGGCCACACAGCCAGAAATTGCAGGGCCCCTAGGAAAAAGGGCTGT
MetValLysCysPheAsnCysGlyLysGluGlyHisThrAlaArgAsnCysArgAlaProArgLysLysGlyCys    204

TGGAAATGTGGAAAGGAAGGACACCAAATGAAAGATTGTACTGAGAGACAGGCTAATTTTTTAGGGAAGATC
TrpLysCysGlyLysGluGlyHisGlnMetLysAspCysThrGluArgGlnAlaAsnPheLeuGlyLysIle     228
                                                                              A
```

IMMUNOCHEMICAL METHOD FOR DETECTION OF ANTIBODY AGAINST HTLV-III CORE PROTEIN BASED UPON RECOMBINANT HTLV-III GAG GENE ENCODED PROTEIN

FIELD OF THE INVENTION

This invention is in the fields of immunology and virology and pertains to immunochemical detection of AIDS virus infection based upon recombinant HTLV-III core antigens.

BACKGROUND OF THE INVENTION

Since the identification of human T cell lymphotropic virus Type III (HTLV-III) (also called lymphadenopathy virus (LAV) or AIDS-associated retrovirus (ARV) as the probable cause of infectious Acquired Immunodeficiency Syndrome (AIDS) and the establishment of a permissive T cell line for mass production of the virus, substantial progress has been made in characterizing the virus. The complete nucleotide sequence of molecular clones of various provirus isolates have been deciphered. See Ratner et al., (1985) Nature 313, 277-284; Wain-Hobson et al., (9185) Cell 40, 9-17; Sanches-Pescador et al., (1985) Science 227, 484-492; Meusing et al., (1985) Nature 313, 450-458. The provirus is 9734-9749 base pairs (bp) in length including two long terminal repeat (LTR) sequences. HTLV-III contains many characteristic structural features of other retroviruses: the long terminal repeats, a core protein gene (gag), a gene region (pol) encoding the virion RNA-dependent DNA polymerase and a gene encoding the virus envelope glycoproteins (env). Unlike other retroviruses the HTLV-III viruses contain two additional small open reading frames (SOR-I and 3'ORF) which may play a role in its unusual cytopathogenicity. See Ratner et al., supra.

HTLV-III gag proteins are synthesized in the from of a polyprotein precursor of 512 amino acids which is proteolytically processed to individual gag proteins p17, p24 and p15. Data obtained from the analysis of nucleotide structure and the gag gene products of HTLV-III and ARV indicate that the p17, p24 and p15 proteins are 134, 230, 122 amino acids long respectively. See Ratner et al., WainHobson et al., Sanches-Pescador et al., and Meusing et al., supra. Two precursors, p70 and p55, have been detected in HTLV-III infected cells in culture and were shown to share peptide homology with the p24 gag protein Roby et al., (9185). Recently the p24 protein has been isolated from HTLV-III. Casey J. M., et al., (1985), J. Virol., 55 (2), 417-423.

Several methods for the detection of HTLV-III infection also have been developed. Solid-phase immunoassays employing inactivated HTLV-III as a whole virus antigen immunoadsorbent have been developed for the detection of antibodies against HTLV-III in sera of patients. Such assays have been shown to detect antibodies in more than 80% of sera from patients with AIDS or AIDS-related complex (ARC), or from individuals infected with HTLV-III and these are useful for diagnosing AIDS and for screening contaminated blood.

Assays employing the whole virus, however, have several drawbacks. Large quantities of the virus must be cultivated as supply for test reagents. Although rigorous safety measures can be instituted, there are dangers associated with large scale cultivation of the infectious virus. Further, there exists a risk, however small, that test reagents prepared with the inactivated virus can be contaminated with live virus. Thus, persons who handle the reagents may be subjected to the risk of HTLV-III infection.

Isolated viral p24 protein has been used in an immunoprecipitation assay for detection of antiHTLV-III antibody in sera of AIDS patients. High serum titer of antibody was found in 73% AIDS patients. Casey, J. M., et al., supra. Assays employing isolated viral component such as the p24 protein, however, do not eliminate the need for production of the virus. Large scale production of the virus is required for isolation of sufficient quantity of the viral protein for preparation of assay reagents.

DISCLOSURE OF THE INVENTION

This invention pertains to recombinant HTLV-III antigenic polypeptides expressed by cloned DNA segments of the gag region of the HTLV-III genome and to immunochemical assays for detecting antibody against HTLV-III core protein employing the polypeptides. The recombinant HTLV-III core proteins are immunoreactive with anti-HTLV-III core protein antibodies in the serum of HTLV-III infected individuals. Because of this, the recombinant core proteins can be used to detect antibodies against HTLV-III core proteins in a biological fluid. In addition, they can be used in conjunction with immunoreactive recombinant HTLV-III envelop proteins for combined assay of antibody against HTLV-III core and envelop protein.

Three HTLV-III recombinant core antigens were expressed in bacterial cells. Restriction fragments of HTLV-III gag gene were cloned into E. coli. (Strain JA221) cells to produces three clonal cell lines. One clonal cell line, designated pG1, produces a hybrid protein containing 13 amino acid residues on the C-terminal of the 17Kd virion protein, the entire p24 polypeptide and 74 amino acid residues of the amino terminal of the 15Kd core ribonucleoprotein. The second clone, pG2, produces a protein similar to pG1 except that it contains no p17 sequences and lacks the $NH_2$-terminal 77 amino acid residues of the p24. The third clone pG3 expresses a protein similar to pG2 except all but 56 amino acids of the C-terminal of p24 are absent. Thus, the antigens are chimeric molecules made up of portions of the virion p17, p24 and p15 core proteins.

The recombinant proteins are expressed by these clones as fusion proteins made up of the HTLV-III polypeptide (encoded by the cloned the gag gene segment) flanked by exogenous (vector supplied) polypeptide elements at the amino and carboxyl terminals. The fusion proteins pG1, pG2 and pG3 are strongly reactive towards anti-gag protein antibodies present present to pooled sera from AIDS patients. The immunoreactivity of the pG1, pG2, and pG3 proteins indicates that strong antigenic determinants are present between amino acid residues 77 and 175 of the viral p24 protein and residues 1 and 74 of the p15 protein.

The bacterially expressed pG2 protein can be purified to virtual homogeneity. This can be accomplished by dissolution of the protein in a buffer containing a strong denaturant (8M Urea) and by subsequent dialysis and repetitive gel filtration chromatography in the presence of the denaturant. The pG2 protein purified by this technique is immunoreactive with antibody in AIDS patient sera. In strip assays, detection of anti-p24 antibody by pG2 protein correlates with detection of the antibody with whole virus.

The recombinant core antigens provide immunochemical methods for detection of antibody against HTLV-III core proteins. Immunochemical assays for detection of antibody against HTLV-III core protein can take several forms, including immunometric assays and antigen sandwich assays. The preferred type of assay is a solid phase immuno metric (double antibody) assay. The purified gag derived polypeptide is immobilized by attaching it to solid phase to form an antigen immunoadsorbent. The immunoadsorbent is used to adsorb anti-HTLV-III core protein antibody in a sample of the biological fluid. The adsorbed anti-HTLV-III antibody is detected with an anti-(human IgG) antibody which is labeled radioisotopically, enzymatically, fluorometrically or in other ways. This second antibody, directed generally against human IgG, binds to anti-HTLV-III antibody adsorbed to the immunoadsorbent and provides a detectable signal which can be evaluated as an indication of the presence of anti-HTLV-III core protein antibody in the sample.

HTLV-III core protein can be used in conjunction with HTLV-III envelop proteins (e.g. HTLV-III polypeptide 121) to enhance detection of antibody against the virus. For this purpose, the approximately equimolar amounts of the core protein (e.g. pG2) and the envelope protein can be affixed to a solid phase to form a dual antigen immunoadsorbent for use in an immunometric assay.

Expression of the pG1, pG2 and pG3 proteins in bacterial cells and demonstration of the immunoreactivity of these proteins establishes that the antigenicity of HTLV-III core proteins can be retained when the proteins are expressed in a host cell system. Further, expression of these proteins enabled identification of certain antigenic regions of p24 and p15 which can aid in rational design of additional recombinant HTLV-III core antigens. For example, other chimeric core proteins which embody these antigenic protein domains can be produced.

Immunochemical assays employing the gag derived polypeptides for detection of anti-HTLV-III core protein antibodies provide several advantages over those based on the whole virus or an isolated viral components. Viral components produced in safe host cells eliminate the need to grow large quantity of the infectious virus for preparation of assay reagents. This alleviates the risk associated with this process. Assay reagents based upon the HTLV-III antigens rather than the whole virus will help mitigate the real or perceived risk of contracting AIDS by technicians who perform the assay. Additionally, homogenous preparations of core protein can provide for less variability in assay performance. In whole virus preparation the level of core protein may vary and affect the sensitivity of the assay.

BRIEF DESCRIPTION OF THE DRAWINGS

FIG. 5 shows the predicted amino acid sequence for the 228 amino acids contained within pG2 protein. The amino acids of the pG3 protein are those amino acids between the marks B and A. The 228 amino acids of the pG2 protein are numbered, each number along the right hand margin referring to the cumulative number of amino acids. The pG3 protein, therefore, encompasses from amino acid 99 (mark B) to number 228 (mark A).

BEST MODE OF CARRYING OUT THE INVENTION

Figure 1:
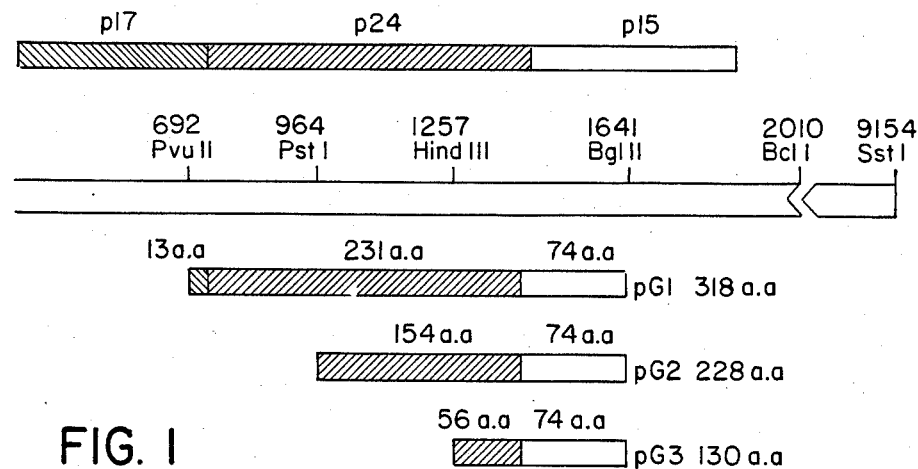
FIG. 1 is a schematic representation of the construction of the HTLV-III gag gene clones

Three recombinant HTLV-III core proteins, designated pG1, pG2 and pG3 were produced by cloning and expressing three segments of DNA from the gag gene of HTLV-III in *E. Coli*. The gag gene of HTLV-III is capable of encoding a protein of 512 amino acid residues. The p17 protein spans amino acid residues 1–132, the p24 is derived from amino acid residues 133–363 and the p15 from amino acid residues 378–512. Amino acids 364–377 are not present in processed, mature viral gag proteins, but are present in pG1, pG2 and pG3 proteins.

The segments were obtained by restriction endonuclease digestion of HTLV-III DNA. HTLV-III DAN was excised by Sst I digestion from λBH-10, a recombinant phage comprising a 9 kb segment of the HTLV-III genome inserted into the vector λgt WESλB. See B. H. Haha et al., *Nature*, 312, 166 (1984). The SstI fragment is shown with the nucleotide numbers above the restriction enzyme designation in FIG. 1.

The pG1, pG2 and pG3 gene constructs were made by further digestion of the Sst I fragment. The three constructs are illustrated schematically in FIG. 1. The Sst I fragment from λBH-10 was digested with the restriction endonucleases Pvu II and Bgl II or Pst I and Bgl II. Pvu II/Bgl II digestion yielded a 949 bp fragment (corresponding to nucleotide 692 through 1641 of the HTLV-III genome) and Pst I/Bgl II digestion gave a 677 bp fragment (nucleotides 964–1641). The fragments were inserted into a the "REV" expression vector (Repligen, Cambridge, Mass.) to give plasmid pG1 and pG2, respectively.

Plasmid pG3 was constructed from pG2. pG2 DNA was digested with Pst I and Hinde III, end repaired and ligated, resulting in excision of the Pst I-Hind III fragment from pG2.

*E. coli* cells were transformed with the recombinant vectors. Bacterial cells containing the plasmids pG1, pG2 and pG3 expressed proteins of 41Kd, 33Kd and 18Kd, respectively. The expressed proteins were fusion proteins containing a methionine residue plus 33 vector encoded amino acid residues at the NH2 terminal of the HTLV-III polypeptide and 14 vector encoded amino acids at the COOH terminal. The fusion proteins were made in large quantities by the transformed bacterial cell lines (over 10% of total cellular protein). The expressed fusion proteins were tested for reactivity with pooled AIDS patient sera by Western blot analysis. Each protein was immunoreactive.

The immunoreactivity of the pG1, pG2 and pG3 proteins indicate that these proteins exhibit strong HTLV-III antigenic determinants. The determinants are present between amino acid residues 77–175 of p24 protein and residues 1–74 of the p15 proteins.

The pG2 protein was purified to greater than 98% homogeneity by the following procedure. Soluble cellular protein was removed from pG2 cell lysates by extraction with a nondenaturant buffer. The fusion protein pG2 was contained in the insoluble cell pellet at approximately 20% purity. The pG2 protein was solubilized by suspending the cell pellet in an extraction buffer comprising 50 nM Tris-HCl, 8 M Urea, 1M NaCl, 10 mM DL dithiothreitol (DTT) and 0.05% EDTA disodium slat. The suspension was homogenized and centrifuged. pG2 in the supernatant was purified by gel filtration chromatography in the extraction buffer, subsequent dialysis against distilled water, and further gel filtration chroma- tography in the extraction buffer. The major peak eluted from final gel filtration column contained the pG2 protein at greater than 98% purity as judged by SDS-PAGE.

Purified pG2 protein was used in a strip immunoassay to characterize sera from healthy individuals in the high risk population and sera from patients with AIDS or ARC. pG2 protein adsorbed onto mitrocellulose strips was incubated with human serum to be tested, washed, then contacted with labeled anti-human IgG to detect antibody bound to the strip. The assay was also performed with disrupted whole virus. pG2 was equally as effective as the whole virus in detecting anti-core protein antibody in sera (100% correlation). Of seropositive healthy homosexuals tested (i.e. those showing antibody reactive with the whole virus), 81% had antibodies reactive with pG2; the percentage dropped to 56% for AIDS and ARC patients.

The pG1, pG2 and pG3 proteins are hybrid proteins containing parts of naturally occurring HTLV-III antigens (i.e. the viral p17, p24 and p15 core proteins). The success achieved in expression of the immunoreactive chimeric core proteins pG1, pG2 and pG3 indicate that the p17, p24 and p15 proteins themselves can be expressed in host cell systems. In addition, other chimeric HTLV-III core proteins, especially proteins which encompass the identified antigenic domains of the virion proteins p24 and p15 can be produced. Further, the DNA segments encoding these polypeptides may be modified (e.g., by deletion, insertion or substitution of nucleotides) to design other HTLV-III core polypeptides. As used herein, the term "recombinant core protein" is intended to be inclusive of all forms of viral core polypeptides which are expressed by genetically engineered host cells and which are immunoreactive with anti-core protein antibody.

Recombinant HTLV-II core proteins, including the pG1, pG2 and pG3 polypeptides, or equivalent type polypeptides can be produced de novo by recombinant DNA techniques. HTLV-III now can be routinely and reproducibly isolated from patients with AIDS and propagated in a line of permissive T cells developed for this purpose. M. Popovic et al. Science 224, 497 (1984); R. C. Gallo et al. Science 224, 500 (1984). From such cells HTLV-III proviral DNA can be obtained and cloned. The designated gag regions of the HTLV-III genome, identified to encode antigenic determinants, can be excised from the proviral DNA (generally by restriction enzyme digestion), inserted into an expression vector, preferably one which can express the polypeptide at high levels, to from a recombinant expression vector containing gag gene sequence. Appropriate host cells transformed by the vector can provide a system for expression of the gene product.

Alternatively, gag DNA segments encoding antigenic regions of the core proteins can be synthesized chemically. Several techniques are available for synthesizing DNA of desired nucleotide sequences. See, e.g., Matteucci et al. *J. Am. Chem. Soc.* (1981) 103:3185; Alvarado-Urbina et al., *Science* (1980) 214:270. Synthesized segments of viral DNA can be adapted and inserted into an expression vector which can be used to transform vector compatible host cells and provide for expression of the gene product.

Core proteins containing the identified antigenic regions of p24 and p15 can be synthesized chemically. The predicted 228 amino acid sequence of the pG2 protein, for example, is shown in FIG. 5; the protein, or proteins, thereof, can be synthesized by the solid phase procedure of Merrifield.

When expressed as heterologous protein in a host cell system, any of several purification techniques, in addition to the techniques described herein for purification of pG2, can be used to purify the recombinant core proteins. For use in immunoassays, the protein must be purified to substantial immunological purity. Importantly, the preparation should be fee of host cell contaminants which might be reactive with antibody in human sera. Such contaminants could yield a high level of false positive results which would detract from the accuracy of the assay.

Immunochemical assays employing the polypeptides can take a variety of forms. The preferred type is a solid phase immunometric assay. In assays of this type, the purified recombinant polypeptide is immobilized on a solid phase to form an antigenimmunoadsorbent. The immunoadsorbent is incubated with the sample to be tested. The duration and conditions of the incubation are standard, those appropriate for the formation of the antigen-antibody complex. The immunoadsorbent is then separated from the sample and a labeled anti-(human IgG) antibody is used to detect human anti-HTLV-III antibody bound to the immunoadsorbent. The amount of label associated with the immunoadsorbent is compared to positive and negative controls to assess the presence or absence of anti-HTLV-III antibody.

The immunoadsorbent can be prepared by adsorbing or coupling purified polypeptide to a solid phase. Various solid phases can be used, such as beads formed of glass, polystyrene, polypropylene dextran or other material. Other suitable solid phases include tubes or plates formed from or coated with these materials.

The recombinant core proteins can be either covalently or non-covalently bound to the solid phase by techniques such as covalent bonding via an amide or ester linkage or adsorption. After the HTLV-III polypeptide is affixed to the solid phase, the solid phase can be post-coated with an animal protein, e.g., 3% fish gelatin. This provides a blocking protein which reduces nonspecific adsorption of protein to the immunoadsorbent surface.

The immunoadsorbent functions to insolubilize anti-core protein antibody in the liquid sample tested. In blood screening for anti-HTLV-III antibody, the immunoadsorbent is incubated with blood plasma or serum. Before incubation, plasma or serum is diluted with normal animal plasma or serum. The diluent plasma or serum is derived from the same animal species that is the source of the anti-(human IgG) antibody. The preferred anti-(human IgG) antibody is goat anti-(human IgG) antibody. Thus, in the preferred format, the diluent would be goat serum or plasma. The optical dilution factor for human plasma and serum is about 10-11 fold.

The conditions of incubation, e.g. pH and temperature, and the duration of incubation are not crucial.

These parameters can be optimized by routine experimentation. Generally, the incubation will be run for 1-2 hours at about 45° C. in a buffer of pH 7-8.

After incubation, the immunoadsorbent and the sample are separated. Separation can be accomplished by any conventional separation technique such as sedimentation or centrifugation. The immunoadsorbent then may be washed free of sample to eliminate any interfering substances.

To assess human antibody bound to the immunoadsorbent, the immunoadsorbent is incubated with the labeled anti-(human IgG) antibody (tracer). Generally, the immunoadsorbent is incubated with a solution of the labeled anti-(human IgG) antibody which contains a small amount (about 1%) of the serum or plasma of the animal species which serves as the source of the anti-(human IgG) antibody. Anti-(human IgG) antibody can be obtained from any animal source. However, goat anti-(human IgG) antibody is preferred. The anti-(human IgG) antibody can be an antibody against the $F_c$ fragment of human IgG, for example, goat anti-(human IgG) $F_c$ antibody.

The anti-(human IgG) antibody or anti-(human IgG)$F_c$ can be labeled with a radioactive material such as $^{125}$Iodine; labeled with an optical label, such as a fluorescent material; or labeled with an enzyme such as horse radish peroxidase. The antihuman antibody can also be biotinylated and labeled avidin used to detect its binding to the immunoadsorbent.

After incubation with the labeled antibody, the immunoadsorbent is separated from the solution and the label associated with the immunoadsorbent is evaluated. Depending upon the choice of label, the evaluation can be done in a variety of ways. The label may be detected by a gamma counter if the label is a radioactive gamma emitter, or by a fluorimeter, if the label is a fluorescent material. In the case of an enzyme label detection may be done colorimetrically employing a substrate for the enzyme.

The amount of label associated with the immunoadsorbent is compared with positive and negative controls in order to determine the presence of anti-HTLV-III core protein antibody. The controls are generally run concomitantly with the sample to be tested. A positive control is a serum containing antibody against HTLV-III core protein; a negative control is a serum from healthy individuals which do not contain antibody against HTLV-III core protein.

For convenience and standardization, reagents for the performance of the immunometric assay can be assembled in assay kits. A kit for screening blood, for example, can include:

(a) an immunoadsorbent e.g. a polystyrene bead coated with a recombinant HTLV-III core polypeptide;

(b) a diluent for the serum or plasma sample, e.g. normal goat serum or plasma;

(c) an anti-(human IgG) antibody e.g. goat anti-(human IgG) antibody in buffered, aqueous solution containing about 1% goat serum or plasma;

(d) a positive control i.e. serum containing antibody against polypeptide 121; and (e) a negative control e.g. pooled sera from healthy individuals which does not contain antibody against polypeptide 121.

If the label is an enzyme, an additional element of the kit can be the substrate for the enzyme.

Another type of assay for anti-HTLV-III antibody is an antigen sandwich assay. In this assay, a labeled HTLV-III recombinant polypeptide is used in place of anti-(human IgG) antibody to detect antiHTLV-III antibody bound to the immunoadsorbent. The assay is based in principle on the bivalency of antibody molecules. One binding site of the antibody binds the antigen affixed to the solid phase; the second is available for binding the labeled antigen. The assay procedure is essentially the same as described for the immunometric assay except that after incubation with the sample, the immunoadsorbent is incubated with a solution of labeled core polypeptide. The HTLV-III polypeptide can be labeled with radioisotope, an enzyme, etc. for this type of assay.

In a third format, the bacterial protein, Protein A, which binds the $F_c$ segment of an IgG molecule without interfering with the antigen antibody interaction can be used as the labeled tracer to detect anti-HTLV-III-antibody adsorbed to the immunoadsorbent. Protein A can be readily labeled with a radioisotope, enzyme, or other detectable species.

Some serum sample appear to show stronger reactivity towards HTLV-III core protein than toward HTLV-III envelop protein. This suggests that combined testing for antibody against both viral core and envelop proteins might enhance the overall sensitivity of a test for HTLV-III infection. The use of the combination of homogenous preparations of recombinant core and envelope protein, rather than the whole virus, for this purpose would eliminate false positives encountered with assays based on preparations of whole virus (which can contain host cell contaminants). This would reduce the waste of valuable blood units.

A combination assay can be used based upon homogenous polypeptide pG2 and recombinant env protein. A suitable HTLV-III env protein is HTLV-III polypeptide 121 described in U.S. patent application Ser. No. 707,606, filed Mar. 1, 1985, the teachings of which are incorporated by reference herein. A mixture of pG2 and polypeptide 121, preferably containing approximately equimolar amounts of the two antigens, can be applied to a solid phase to form a double antigen immunoadsorbent for adsorption of antibody against either antigen. The assay would be conducted in the same manner as that described for the pG2 assay above.

Immunochemical assays employing recombinant HTLV-III core proteins for detection of antibodies against HTLV-III core protein have several advantages over those employing a whole (or disrupted) virus for this purpose. For one, assays based upon the polypeptide will alleviate the concern over growing large quantities of infectious virus and the inherent variability associated with cell culturing and virus production. Efficient expression of viral antigens in *E. coli.* as other host cell systems provide a safe means of large scale production of assay reagents. Further, the assay will help mitigate the real or perceived fear of contracting AIDS by technicians in hospitals, clinics and blood banks who perform the test. As mentioned, reagents for assays based upon the whole virus (e.g. whole virus antigen immunoadsorbent), even through they are made with a disrupted, inactivated virus, present a risk of contamination with live virus. For example, a possible source of live virus contamination may be residual cell debris from the virus isolation process. Although extensive precautions can be taken to reduce the risk of contamination, it is virtually impossible to completely eliminate it. Significantly, the risk, though minimal, may be perceived as greater than it actually is by persons who handle the test reagents. Assay reagents without whole virus can help minimize this perception of risk. Immunoassays based upon viral components in safe host cell systems provide a substitute for assays based on the whole virus which are at least comparable in sensitivity and specificity and superior in reproducibility.

Assays employing natural, isolated HTLV-III core proteins, e.g. p24 protein, while they eliminate the use of whole virus from assay reagents, still require the growth of the virus on a large scale for a supply of the natural protein and thus do not eliminate the risks attendant to this procedure.

The invention is illustrated further by the following Exemplifications.

EXEMPLIFICATION

Bacterial strains and plasmids

E. coli strain JA221 (1pp−) was used in all experiments as the host cell. Ghrayeb et al. (1984) EMBO J. 3. 2437-2442. Cells were grown in L-Broth supplemented with ampicillin (100 μg/ml). The REV (Repligen, Cambridge, MA) expression vector was used for clongin of the HTLV-III DNA.

DNA manipulations

Isolation of plasmid DNA and various manipulations were carried out as previously described by L.C. Ghrayeb et al., i.e. supra. Restriction enzymes were obtained from New England Biolabs. T4 DNA ligase was purchased from Boehringer Mannheim Biochemicals. The DNAs were digested with restriction enzymes in conditions described by the manufacturer.

Expression and analysis of the gag gene clones

HTLV-III gag proteins produced by recombinant clones PG1, PG2 and PG3 were analyzed by SDS-polyacrylamide gel electrophoresis (SDS-PAGE) as described previously. See Chang, N. T. et al., (1985), Science, 228, 93–96. Cells were grown in 1 ml L-broth at 37° C. overnight and the cells were harvested by centrifugation at 5000×g for 10 minutes. The cell pellets were dissolved in 200 μl of loading buffer and 20 μl was applied to a 12% SDS-polyacrylamide gel and electrophoresed under reducing conditions. Unlabeled molecular weight markers were obtained from Biorad Laboratories. [$^{14}$C]-labeled molecular weight markers were obtained from Amersham. The expression of HTLV-III specific protein by the recombinant clones was detected by Western blotting analysis using sera from AIDS patients. Bacterial proteins were separated on a 12% SDS-polyacrylamide gel and transferred to nitrocellulose and blotted as described below. The blot was incubated overnight at 4° C. with sera from AIDS patients or from healthy individuals. After washing, virus specific protein bands were visualized by incubation with [$^{125}$I]-labeled goat antihuman IgG (see below). The blots were air dried and exposed to Kodak X-AR5 at −70° C. with intensifying screens.

Purification of the pG2 protein

For large scale growth, 20 ml of an overnight culture of pG2 were inoculated into 1 liter of L-Broth containing 100 μg/ml of ampicillin and 0.025% antifoam, and shaken at 37° C. The cells were harvested after 8 hr and washed with 50 mM Tris-HCl pH 8.5 (sonication buffer). 25 g of cell pellet were suspended in 70 ml of sonication buffer and sonicated in two portions at 70 W for eight 30 sec bursts with a 60 sec cooling period between each burst. The lysed cells were then centrifuged at 10,000×g for 30 min. All of the pG2 protein was found in the pellet and constituted approximately 20% of the total protein as judged by SDS-PAGE.

The pellet containing the pG2 protein was suspended in 50 nM Tris-HCl pH 8.5 containing 8M Urea, 1M NaCl, 10 nM DL dithiothreitol (DTT) and 0.05% EDTA disodium salt (extraction buffer). The suspension was incubated at 45° C. for 60 min and centrifuged at 10,000×g for 30 min. The resulting supernatant was applied to a Sephacryl S-300 gel filtration column (5×80 cm) previously equilibrated with extraction buffer containing 5 mM DTT. The column was eluted in the same buffer at a flow rate of 0.5 ml/min at room temperature and the fractions (10 ml) were monitored by U.V. absorption at 280 nm. The pG2 protein, found in the second main peak, was pooled and dialyzed exhaustively against distilled water at 4° C. During dialysis the pG2 protein was precipitated quantitatively. The precipitated protein was then redissolved in 10 ml of extraction buffer containing 10 mM DTT and incubated at 45° C. for 30 min. The resulting solution was applied to a second Sephacryl S-300 column (2.6×65 cm) under identical conditions to the first column. The major peak contained the pG2 protein which was 95% pure as judged by SDS-PAGE. The protein was further purified by repeating the second column purification under identical conditions. The main peak from the third S-300 column contained the pG2 protein in 98% purity. The yield was 50 mg and this preparation was used for screening human sera (see below).

Immunoreactivity of pG2 with Human Sera

50 μg of pure pG2 protein or 430 μg of purified disrupted HTLV-III virus, were electrophoresed on a 12% SDS polyacrylamide gel (13 cm×13 cm×1.5 mm) and transferred to nitrocellulose using a Biorad Tran-Blot apparatus. The electroblotting buffer used was 20% aqueous methanol containing 0.016M Tris base and 0.13M glycine, and transfer was performed at 40 volts at 4° C. overnight. The nitrocellulose paper was then shaken for 2 hr at 37° C. with 60 ml of PBS containing 5% non-fat dry milk, 0.11% sodium azide and 0.1% antifoam (milk buffer) and then for 2 hrs at room temperature with 60 ml of 5% normal goat serum in milk buffer. At this stage, the blocked nitrocellulose was either stored at −20° C., or used directly for the strip assay. The nitrocellulose was cut into 13 cm×0.5 cm strips, and each strip was rocked overnight at 4° C. with 4 ml of milk buffer containing 5% normal goat serum and 40 μl of the human serum to be tested in a 15 ml disposable conical tube. The next day the milk solution was replaced with 10 ml of 0.15% sodium deoxycholate, 0.1M NaCl, 0.5% triton X-100, 0.1 mM phenylmethylsulfonyl fluoride in 10 mM sodium phosphate pH 7.5 (wash buffer) and the tubes were rocked for 1 hr. The wash buffer was removed and replaced with 4 ml 5% goat serum in milk buffer and the tubes were rocked for 1 hr, at which time $^{125}$[I]-labeled goat anti-human IgG (10$^6$ cpm/ml) was added. After 30 min, the strips were washed for 1 hr with 10 ml of wash buffer, air dried and exposed to Kodak XAR-5 film at −70° C. with intensifying screens.

Radioimmunoassay 96 well microtiter dishes were coated with the antigen at 100 μg/ml in 50 mM Tris-HCl pH 8.0. After an overnight incubation, the wells were washed three times with phosphate buffered saline (PBS). The wells were then post coated with 200 μl 3% fish gelatin (Norland Products, Inc.) in PBS containing 0.1% sodium azide. The fish gelatin solution was removed and each well was filled with 200 μl of 1:5 or 1:10 dilutions of the test serum in PBS containing 10% normal goat serum, 10% anti-$E.$ $coli$ goat serum and 1% fish gelatin. After one hour at room temperature, the wells were washed three times with PBS and 20 μl of [$^{125}$I]-labeled goat anti-human IgG (Fc portion) in 1% normal goat serum, 1% fish gelatin in PBS at $1.5 \times 10^6$ cpm/ml was added to each well. After one hour at room temperature, the plates were washed four times with PBS and once with distilled water and counted.

RESULTS

Construction of the HTLV-III gag gene clones

The isolation of recombinant phage clone BH10 containing the unintegrated linear form of HTLV-III proviral DNA has been reported previously. Shaw et al., (1985) $Science$, 226, 1165-1171. The 9 Kb HTLV-III insert of phage BH10 was released by SstI cleavage within the R element of the LTR (See FIG. 1). The SstI fragment was then digested with either PvuII and BglII or PstI and BglII. The 949 bp PvuII-BglII fragment and the 677 bp PstI-BglII fragments were inserted into the REV expression vector (Repligen, Cambridge, Mass.) to give pG1 and pG2 respectively (FIG. 1). Clone pG3 was constructed from pG2. pG2 DNA was digested with PstI and HindIII, end repaired and ligated. Thus, in pG3 the PstI-HindIII fragment was deleted from the HTLV-III DNA (insert of pG2. As seen from FIG. 1, the three constructs carry HTLV-III DNA that is predicted to code for chimeric peptides containing various portions of the p17, p24 and p15 viral gag proteins. See Ratner et al., (1985), $Nature$, 313, 277-284. The sizes of the expressed proteins are larger than predicted since the expression vector supplies the initiation methionine codon plus 35 amino residues at the NH$_2$-terminus of each expressed protein.

Figure 2:
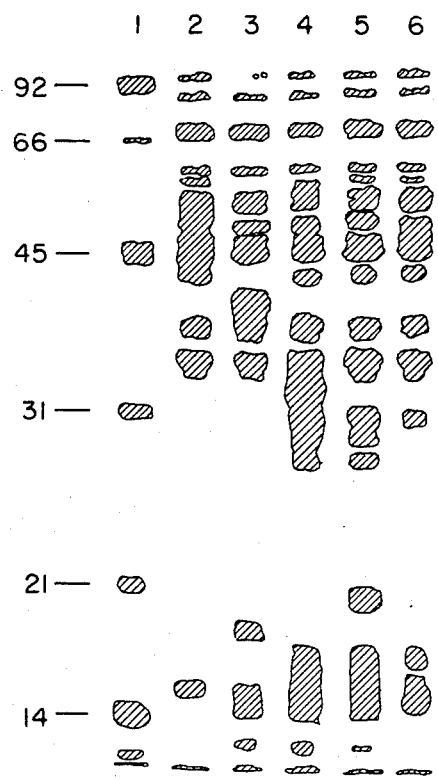
FIG. 2 shows SDS-PAGE analysis of HTLV-III gag gene hybrid proteins, pG1, pG2 and pG3.

Expression of the HTLV-III gag gene clones $E.$ $coli$ transformed with plasmids, pG1, pG2 or pG3 were found to produce proteins of 41kd, 33kd and 18kd, respectively, as demonstrated by SDS-polyacrylamide gel electrophoroesis of total bacterial cell lysates. SDS-PAGE analysis of HTLV-III gag gene proteins is shown in FIG. 2. Cells from 1 ml cultures were centrifuged and the pellets resuspended in 200 μl of SDS sample buffer and analyzed by SDS-PAGE as describe above. 20 μl of cell lysate were loaded per lane and gels were strained with commassie brilliant blue R250. (Lane 1, molecular weight markers, lane 2, control cells with no plasmid, lane 3, pG1, lane 4, pG2, lane 5, pG3, lane 6, cells carrying the REV vector containing no HTLV-III DNA. The number on the left designate the molecular weights in kilodaltons.)

All three proteins were made in large quantitied (over 10% of total cellular protein in these cells) but were not detected in the host cell with or without the REV vector alone. The overproduction of the plasmid encoded HTLV-III gag proteins caused a marked decrease in the rate of cell growth. The kinetics of the growth rate could be correlated with the accumulation of the gag gene products in the cytoplasm although no cell lysis was observed (data not shown). Maximum accumulation was observed at 8 hours after the start of the log phase growth period. In addition, the expressed gag gene products were present as aggregates containing membrane proteins after disruption of the cells. Depending on growth conditions, HTLV-III gag proteins of smaller size could be detected on SDS-PAGE gels (FIG. 2). The products are likely due to the degradation of the major high molecular weight gag proteins with increasing growth time.

Immunochemical characterization of the gag gene products

Figure 3:
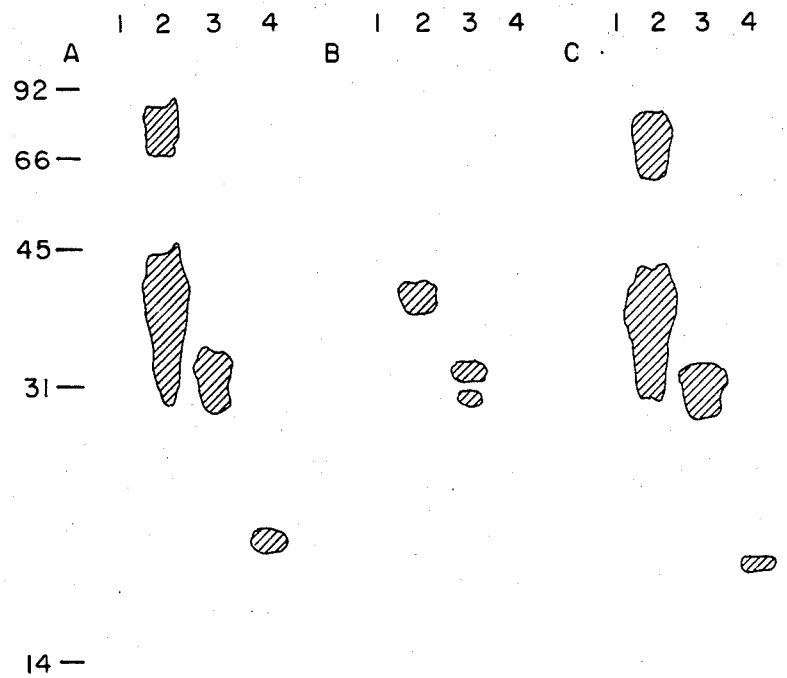
FIG. 3A shows a Western blot analysis of the immunoreactivity of the pG1, pG2 and pG3 HTLV-III gag gene clones.

The bacterial expressed HTLV-III gag-specific protein in cells carrying pG1, pG2 or pG3 were detected by Western blot analysis using sera pooled from AIDS patients. The results of this analysis are shown in FIG. 3. SDS-PAGE analysis was performed exactly as in FIG. 2. Transfer of proteins to nitrocellulose paper, reaction with antibodies and detection of immunoreactive bands is described above. FIG. 3A shows a blot in which lane 1 is control cells, lane 2 is pG1, lane 3 is pG2 and lane 4 is pG3. The blot was treated with pooled sera from AIDS patients. The numbers on the left designate the relative position of the [$^{14}$C] molecular weight markers that were run along with the samples in lanes 1–4, but are not shown in the figure. The result clearly shows the synthesis of specifically cross-reacting HTLV-III peptide in recombinant clones containing pG1, pG2 and pG3. The immunoreactive proteins in each clone correspond to the expressed proteins, 41kd, 33kd, 18kd, seen in the Coomassie blue stained SDS-polyacrylamide gel (FIG. 2). There was no HTLV-III virion-specific peptide detected in lysate of control JA221 cells.

Figure 4:
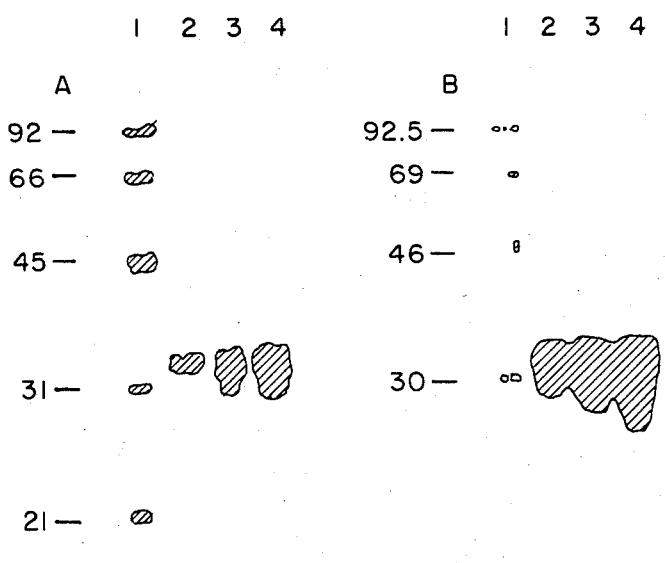
FIG. 4 shows SDS-PAGE analysis of purified pG2.

The products of pG2 was purified to greater than 98 homogeneity as judged by SDS-PAGE. FIG. 4 shows SDS-PAGE analysis of pG2 purified as described above. PG-2 protein eluted from a sphacryl S-300 column in 50 mM Tris-HCL pH 8.5 containing 8M Urea, 1M NaCl and 5 mM DTT, was mixed with an equal volume of 2× SDS-PAGE sample buffer, heated at 100° C. for 5 min and applied to two identical 12% SDS-PAGE gels. One of the gels was stained with Coomassie Brilliant Blue (panel A), while the other transferred to nitrocellose and the blot treated with pooled sera from AIDS patients (panel B) as in FIG. 3. Panel A, lane 1 is molecular weight markers, lane 2, 3, 4 are pure pG2 at 2, 5, and 10 g respectively. Panel B is identical to A except that lane 1 was run with $^{14}$[C]-labeled molecular weight markers.

The major band is of 33 kd while there is a minor band of 30 kd which is also seen in total cell lysates (FIG. 2) and is more likely a degradation product. A very minor band of 65 kd can also be seen and is most likely to be the dimer form of pG2. All the bands that are visible by Commassie blue staining are also immunoreactive towards HTLV-III specific antibodies present in sera from AIDS patients (FIG. 4B) as well as the anti-P24 mouse monoclonal antibody (data not shown). We feel confident that the pG2 protein is essentially free of contaminating $E.$ $coli.$ proteins.

The purified pG2 protein was used to screen for antibodies directed towards the core p24 protein in human sera, using a strip assay based on the western blot technique. The same samples were also tested under identical conditions, using the purified, disrupted HTLV-III virus. The results are summarized in Table 1.

TABLE 1

| Clinical Status | No. Tested | No. Positive For p24 of HTLV-III | No. Positive Using pG2 |
|---|---|---|---|
| Healthy donors | 50 | 0 | 0 |
| Healthy homosexuals* | 49 | 17 | 17 |
| ARC** | 51 | 28 | 28 |
| AIDS** | 34 | 19 | 19 |

*Only 21 of these donors were seropositive for antibodies to either p24 and/or gp41 of HTLV-III. In addition, the same individuals who were positive for p24 antibodies using the whole virus assay were also positive for antibodies to pG2.
**All these sera were positive for antibodies to gp41.

The results show that there is 100% correlation between p24 antibodies detected by pG2 protein and those detected by the whole virus. In addition, none of the normal donor controls were reactive with pG2 protein. This indicates the recombinant pG2 protein can substitute adequately for the whole virus when detection of p24 antibodies is required. The data presented in Table 1 also show that of the 21 seropositive healthy homosexuals tested, 17 (81%) had detectable antibodies to the p24. In both ARC and AIDS patients, the percentage drops to 56%. Whether the anti-p24 antibody titer is an indication of the progress of HTLV-III infection remains to be studied. In this regard, the uses of pG2 protein in such studies would be preferable since the levels of p24 protein in different virus preparations may vary and may affect the sensitivity of the assay.

Figure 6:
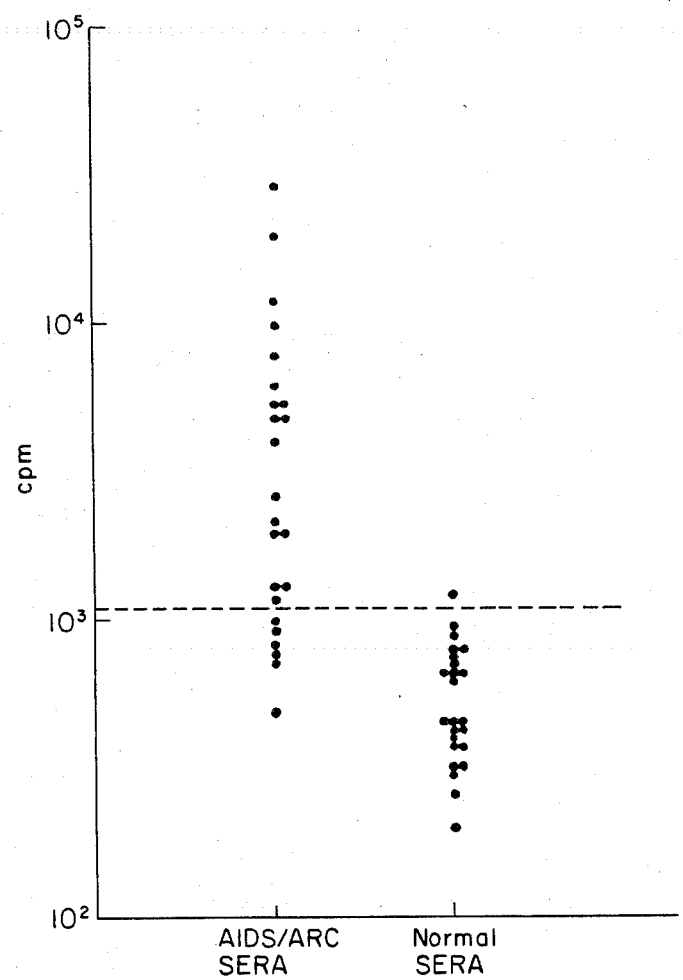
FIG. 6 illustrates RIA results for antibodies against purified pG2 protein in sera from AIDS/ARC patients and healthy individuals.

Partially purified pG2 protein was tested in a solid phase RIA. Details of the plate RIA assay are given above. The pG2 protein preparation used was only "partially" purified. 24 sera from AIDS/ARC patients and 24 sera from healthy individuals were used in the assay and results were plotted on a semi-log scale. The horizontal dotted line designates the cut-off points so that values below the line are considered negative while those above are considered positive. The results are shown in FIG. 6. The results indicated that 18 out of the 24 AIDS or ARC patients' sera tested were reactive with the antigen. The 6 sera from patients with AIDS or ARC that were negative in the RIA assay were found to contain no detectable amounts of anti-p24 antibodies as assayed by a strip immunoassay base on Western blot technique using the purified disrupted whole virus (data not shown). Of the 24 normal human sera tested in the RIA, only one was positive but was negative when tested with the purified virus in a Western blot (data not shown). The reactivity of the one normal sample may be due to the presence of unusually high titre of anti-*E. coli* antibodies present in that particular serum and the fact that the pG2 antigen preparation contained trace amounts of *E. coli* protein impurities. This nonspecific immunoreactivity can be eliminated by absorption of this serum with Sepharose 4B conjugated with *E. coli* extract. Alternatively, better purified pG2 preparations such as the preparation used in the strip assay can be used.

Equivalents

Those skilled in the art will recognize, or be able to ascertain no more than routine experimentation, many equivalents to the specific embodiments of the invention described herein. Such equivalents are intended to be encompassed by the following claims.

We claim:

1. A method of detecting antibody against HTLV-III core protein in a biological fluid, comprising the steps of:

a. providing an antigen immunoadsorbent comprising a solid phase to which is attached a HTLV-III core antigen which is a chimeric antigen comprising an amino acid sequence beginning at amino acid number 1 through 99, and extending to amino acid number 228, as shown in FIG. 5, the chimeric antigen being immunoreactive with antibody against HTLV-III core protein;

b. incubating the immunoadsorbent with a sample of the biological fluid to be tested under conditions which allow antibody in the sample to complex with the antigen immunoadsorbent;

c. separating the immunoadsorbent from the sample; and d. determining antibody bound to the immunoadsorbent as an indication of antibody against HTLV-III core protein in the sample.

2. A method of claim 1, wherein the HTLV-III antigen is the pG2 polypeptide having an amino acid sequence substantially as shown in FIG. 5.

3. A method of claim 1, wherein the biological fluid is human sera or plasma.

4. A method of claim 1, wherein the step of determining the antibody bound to the immunoadsorbent comprises:

(a) incubating the immunoadsorbent with a labeled antibody against immunoglobulin of the species from which the biological fluid is derived;

(b) separating the immunoadsorbent form the labeled antibody; and (c) detecting the label associated with the immunoadsorbent as an indication of antibody against HTLV-III core protein in the sample.

5. A method of claim 4, wherein the biological fluid is human plasma or serum, and the labeled antibody is labeled anti-human IgG antibody.

6. A method of detecting antibody against HTLV-III core protein in human plasma or serum, comprising the steps of:

(a) providing an antigen immunoadsorbent comprising a polystyrene bead coated with an essentially homogeneous preparation of pG2 polypeptide having the amino acid sequence substantially as shown in FIG. 5;

(b) incubating the immunoadsorbent with a sample of human plasma or serum under conditions which permit anti-HTLV-III core protein antibody in the sample to complex with the pG2 polypeptide;

(c) separating the immunoadsorbent from the sample;

(d) incubating the immunoadsorbent with a solution of labeled anti-human Ig antibody;

(e) separating the immunoadsorbent from the solution of labeled antibody; and (f) detecting the label associated with the immunoadsorbent as an indication of anti-HTLV-III core protein antibody in the sample.

7. An immunoadsorbent comprising a solid phase support having attached thereto a HTLV-III core protein which is a chimeric antigen, comprising an amino acid sequence beginning at amino acid number 1 through 99, and extending to amino acid number 228, as shown in FIG. 5, the chimeric antigen being immunoreactive with antibody against HTLV-III core protein.

8. An immunoadsorbent of claim 7, wherein the recombinant HTLV-III core protein is pG2 polypeptide having the amino acid sequence substantially as shown in FIG. 5.

9. An assay for antibody against HTLV-III in a biological fluid comprising the steps of:
   a. providing an immunoadsorbent comprising a solid phase to which is attached mixture of
      (i) HTLV-III core protein which is a chimeric antigen, comprising an amino acid sequence beginning at amino acid number 1 through 99, and extending to amino acid number 228, as shown in FIG. 5, the chimeric antigen being immunoreactive with antibody against HTLV-III envelope protein immunoreactive with antibody against HTLV-III envelope protein;
   (b) incubating the immunoadsorbent with a sample of biological fluid;
   (c) separating the immunoadsorbent from the sample; and
   (d) determining antibody bound to the immunoadsorbent as an indication of antibody against HTLV-III in the sample.

10. An assay for antibody against HTLV-III in a biological fluid, comprising the steps of:
   (a) providing an immunoadsorbent comprising a solid phase to which is attached approximately an equal amount of pG2 polypeptide having the amino acid sequence substantially as shown in FIG. 5 and HTLV-III polypeptide 121;
   (b) incubating the immunoadsorbent with a sample of biological fluid;
   (c) separating the immunoadsorbent from the sample; and
   (d) incubating the immunoadsorbent with a solution of anti-human Ig antibody;
   (e) separating the immunoadsorbent from the sample;
   (f) detecting the label associated with the immunoadsorbent as an indication of anti-HTLV-III antibody in the sample.

11. An immunoadsorbent comprising a solid phase coated with an equal amount of pG2 polypeptide having an amino acid sequence substantially as shown in FIG. 5 and polypeptide 121.

12. A HTLV-III core antigen immunoreactive with antibody against HTLV-III core protein the antigen comprising an amino acid sequence beginning at amino acid number 1 through 99, and extending to amino acid number 228, as shown in FIG. 5.

13. PG2 polypeptide having the amino acid sequence substantially as shown in FIG. 5.

14. An essentially homogeneous preparation of pg2 of claim 13 which is 98% pure protein.

15. A method of detecting antibody against HTLV-III core protein in a biological fluid, comprising the steps of:
   (a) providing an antigen immunoadsorbent comprising a solid phase to which is attached an HTLV-III core antigen immunoreactive with antibody against HTLV-III core protein, the HTLV-III core antigen comprising an amino acid sequence beginning at amino acid number 1 through 99, and extending to amino acid number 228, as shown in FIG. 5;
   (b) incubating the immunoadsorbent with a sample of the biological fluid to be tested under conditions which allow antibody in the sample to complex with the antigen immunoadsorbent;
   (c) separating the immunoadsorbent from the sample; and
   (d) determining antibody bound to the immunoadsorbent as an indication of the antibody against HTLV-III core protein in the sample.

16. A kit for detecting antibody against HTLV-III core protein in biological fluids, comprising, in separate containers, the components:
   a. an immunoadsorbent coated with a HTLV-III core polypeptide which is a chimeric antigen, comprising an amino acid sequence beginning at amino acid number 1 through 99, and extending to amino acid number 228, as shown in FIG. 5, the chimeric antigen being immunoreactive with antibody against HTLV-III core protein; and
   b. an anti-(human IgG) antibody.

17. A kit of claim 16, wherein the HTLV-III core protein has the amino acid sequence substantially as shown in FIG. 5.

18. A kit of claim 16, further comprising:
   (a) a diluent for the biological fluid;
   (b) a positive control solution; and
   (c) a negative control solution.

19. A kit of claim 18, wherein the positive control solution is serum containing antibody against polypeptide 121 and the negative control solution is sera that does not contain antibody against polypeptide 121.

20. A method of detecting antibody against HTLV-III core protein in a biological fluid, comprising the steps of:
   a. providing an antigen immunoadsorbent comprising a solid phase to which is attached a chimeric HTLV-III core antigen immunoreactive with antibody against HTLV-III core protein, the chimeric antigen comprising an amino acid sequence beginning at amino acid number 1 through 99, and extending to amino acid number 228, as shown in FIG. 5;
   b. incubating the immunoadsorbent with a sample of the biological fluid to be tested under conditions which allow antibody in the sample to complex with the antigen immunoadsorbent;
   c. separating the immunoadsorbent from the sample; and
   d. determining antibody bound to the immunoadsorbent as an indication of antibody against HTLV-III core protein in the sample.

21. A method of claim 20, wherein the polypeptide is pG2 having the amino acid sequence substantially as shown in FIG. 5.

* * * * *